United States Patent [19]

Meitzler et al.

[11] Patent Number: 5,361,035
[45] Date of Patent: Nov. 1, 1994

[54] RESONANT CAVITY FLEXIBLE FUEL SENSOR AND SYSTEM

[75] Inventors: Allen H. Meitzler, Ann Arbor; George S. Saloka, Dearborn, both of Mich.

[73] Assignee: Ford Motor Company, Dearborn, Mich.

[21] Appl. No.: 184,756

[22] Filed: Jan. 21, 1994

Related U.S. Application Data

[63] Continuation of Ser. No. 833,691, Feb. 11, 1992, abandoned.

[51] Int. Cl.$^5$ ............................................. F02B 75/12
[52] U.S. Cl. ................................... 324/663; 73/61.43
[58] Field of Search ............... 73/61.79, 61.49, 61.43; 324/663–670, 675, 682, 448; 123/1 A, 575

[56] References Cited

U.S. PATENT DOCUMENTS

| | | | |
|---|---|---|---|
| 3,231,815 | 1/1966 | Spencer | 324/675 |
| 4,438,749 | 3/1984 | Schwippert | |
| 4,453,125 | 6/1984 | Kimura et al. | |
| 4,540,936 | 9/1985 | Walsh | 324/668 |
| 4,559,493 | 12/1985 | Goldberg et al. | 324/668 |
| 4,594,968 | 6/1986 | Degobert et al. | |
| 4,706,630 | 11/1987 | Wineland et al. | |
| 4,770,129 | 9/1988 | Miyata et al. | |
| 4,862,060 | 8/1989 | Scott et al. | 73/61.49 |
| 4,905,655 | 3/1990 | Maekawa | 73/861.08 |
| 4,909,225 | 3/1990 | Gonze et al. | |
| 4,915,084 | 4/1990 | Gonze | |
| 4,939,467 | 7/1990 | Nogami et al. | |
| 4,945,863 | 8/1990 | Schmitz et al. | |
| 4,971,015 | 11/1990 | Gonze | |
| 4,974,552 | 12/1990 | Sickafus | |
| 5,005,402 | 4/1991 | Pischinger | 324/663 |
| 5,091,152 | 2/1992 | Thomas, Jr. | 324/448 |
| 5,134,381 | 7/1992 | Schmitz et al. | 324/663 |
| 5,182,523 | 1/1993 | Ertel et al. | 73/61.43 |

FOREIGN PATENT DOCUMENTS 7712689 5/1979 Netherlands ................ 123/1 A

OTHER PUBLICATIONS

Wiszler, "Automatic Control of Internal Combustion Engines Operating on Gasoline/Alcohol Mixtures by Means of Electronic Systems" a doctoral dissertation presented to the faculty of Heidelberg University, Germany, Jul. 1983.
"Information and Data on alcohol Sensor", Japan Electronic Control Systems Co., ltd. (1988).
Hayt, Jr., Engineering Electromagnetics, 5th Edition, McGraw-Hill Book Company, 1989, pp. 417–426.
Schmitz and Siedentop, "Intelligent Alcohol Fuel Sensor", SAE Paper No. 900231.
"Methanol Sensor", distributed by Japan Electronic Control Systems Co., Ltd. at SAE Convergence Meeting, Oct., 1990.

*Primary Examiner*—Robert Raevis
*Attorney, Agent, or Firm*—Allan J. Lippa; Roger L. May

[57] ABSTRACT

A flexible fuel sensor is disclosed where two concentric conductors, adapted to receive the fuel mixture, are shorted to provide a resonant electromagnetic cavity.

7 Claims, 2 Drawing Sheets

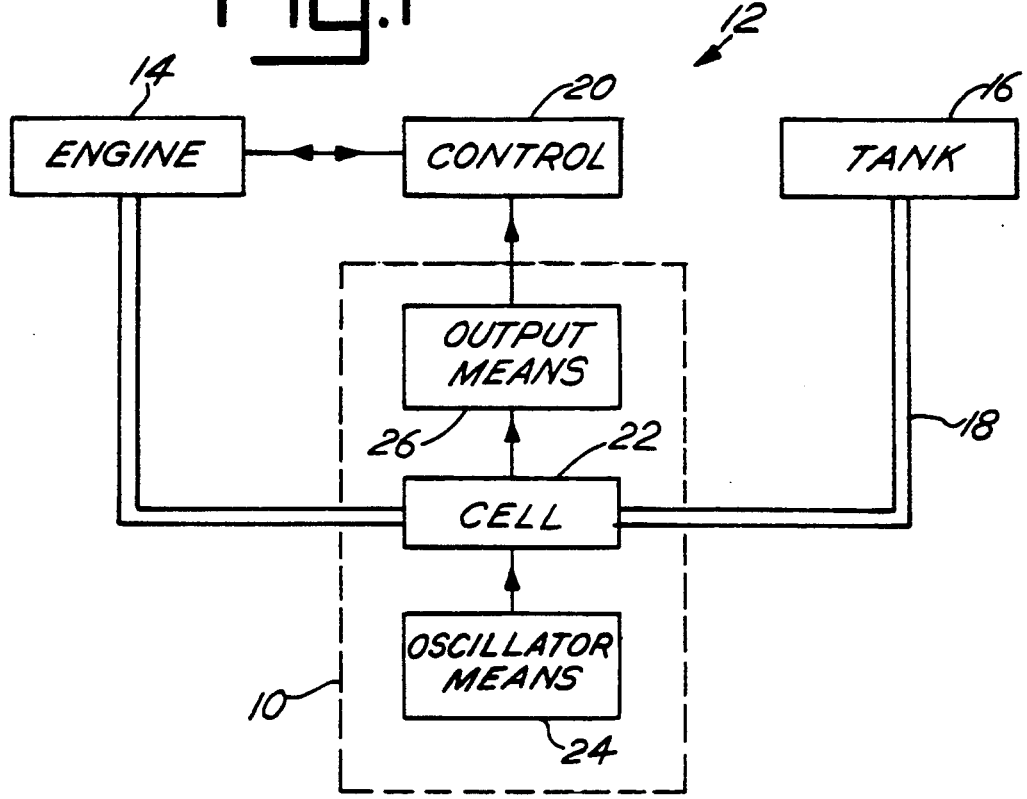
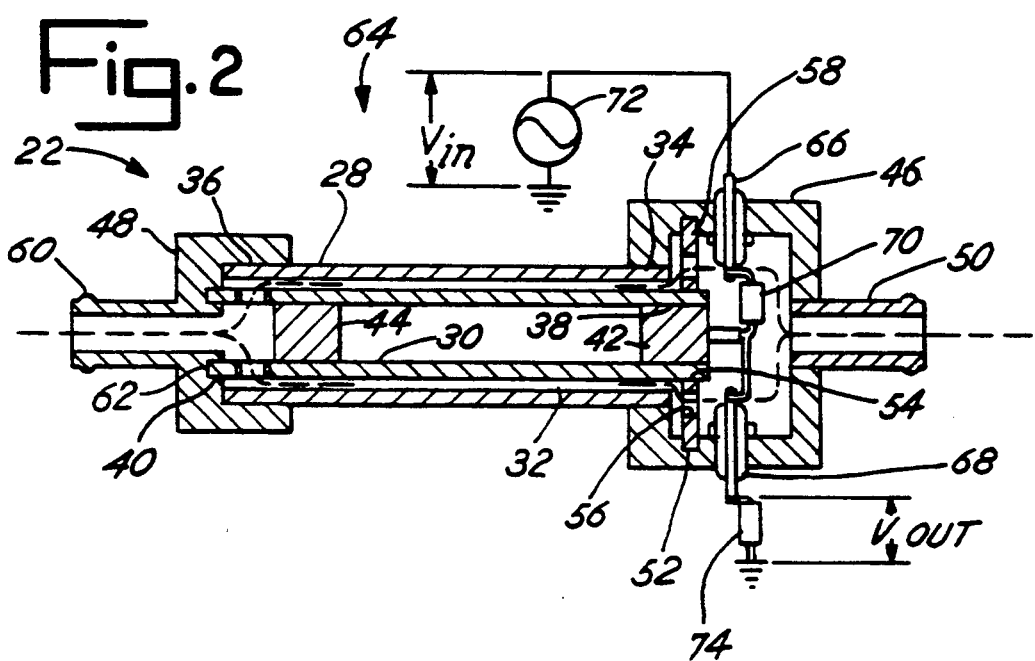

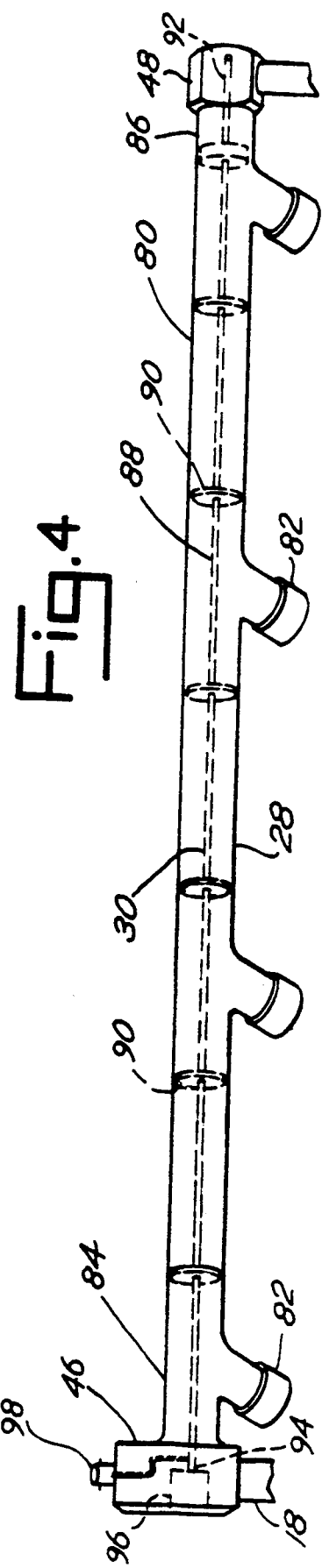
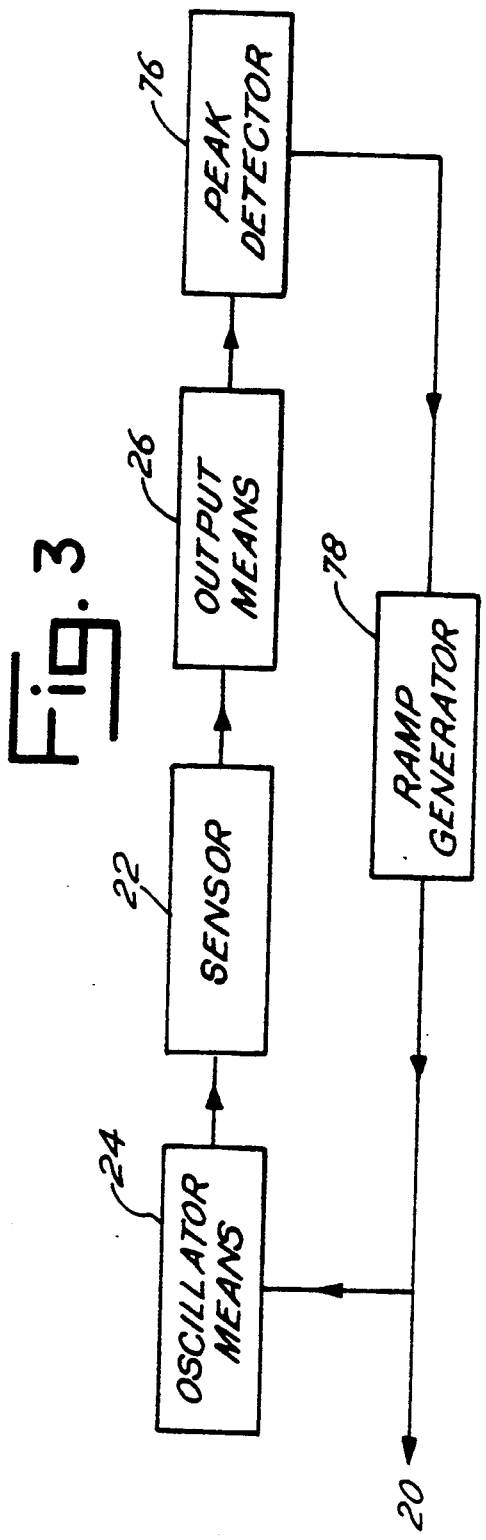

RESONANT CAVITY FLEXIBLE FUEL SENSOR AND SYSTEM

This application is a continuation application of Ser. No. 07/833,691, filed Feb. 11, 1992, now abandoned.

BACKGROUND OF THE INVENTION

The present invention relates generally to a flexible fuel system and more particularly to a flexible fuel sensor using a resonant electromagnetic cavity to determine fuel composition.

The interest in flexible fuel vehicles has increased dramatically in recent years. This is especially true with respect to vehicles capable of operating on blends of gasoline and alcohol.

In such vehicles, it is necessary to monitor the fuel mixture (e.g., the percentage by weight of alcohol) in order to adjust engine performance. The signal from the flexible fuel sensor is typically transmitted to and utilized by an electronic engine control to properly set spark timing, exhaust gas recirculation and fuel enrichment. The flexible fuel system plays a particularly important role during open-loop feedback conditions, i.e., cold start-up and wide-open throttle.

The flexible full sensors presently under investigation fall into two major categories: optical effect and dielectric effect. Optical sensors utilize the index of refraction or infrared absorption pattern of the fuel blend. Dielectric sensors operate upon a change in the dielectric constant of the fuel blend as the fuel mixture varies.

SUMMARY OF THE INVENTION

In a principal aspect, the present invention is a flexible fuel sensor, i.e., a sensor for use in determining the fuel mixture of at least two liquid fuels. The present invention has particular application to gasoline/methanol blends.

The flexible fuel sensor includes a pair of substantially concentric conductors, electrically shorted at one end thereof. The two liquid fuels flow between the conductors. The sensor thereby defines and provides a resonant electromagnetic cavity, through which the liquid fuel mixture flows, having an electrical resonant frequency dependent upon the fuel mixture. In the system context, the resonant electromagnetic cavity is coupled to and driven by an oscillator. A content signal representative of the fuel mixture is responsively developed.

It is thus an object of the present invention to provide a flexible fuel system and sensor. Another object is a flexible fuel system for controlling vehicle operation in accordance with the fuel mixture as monitored and determined by a resonant electromagnetic cavity. Still another object is a reliable, yet inexpensive flexible fuel sensor.

It is also an object of the present invention to provide a flexible fuel sensor defining a resonant electromagnetic cavity which resonates at a frequency dependent upon the fuel mixture. A further object is a resonant electromagnetic cavity sensor including two substantially cylindrical, substantially coaxial conductors. Yet another object is a two-conductor resonant cavity sensor wherein the fuel rail of the vehicle functions as the outer conductor.

These and other features, objects and advantages of the present invention are set forth or implicit in the following description of certain preferred embodiments.

BRIEF DESCRIPTION OF THE DRAWING

Preferred embodiments of the present invention are described, in detail, with reference to the drawing wherein:

FIG. 1 is a schematic representation of a flexible fuel vehicle incorporating a first preferred embodiment of the present invention;

FIG. 2 is a partial cross-sectional view of the flexible fuel sensor of FIG. 1;

FIG. 3 is a schematic representation of a second preferred embodiment; and

FIG. 4 is a side view of a fuel line and rail illustrating a third preferred embodiment of the present invention.

DETAILED DESCRIPTION OF PREFERRED EMBODIMENTS

Preferred embodiments of the present invention are shown in FIGS. 1–4, wherein common reference numerals are utilized. Referring first to FIGS. 1 and 2, the present invention is shown as a flexible fuel system, generally designated 10, for a flexible fuel vehicle 12 having an engine 14, fuel tank 16, fuel line 18 and electronic engine control 20. As is well known, the engine control 20 regulates certain parameters of engine performance based upon the fuel mixture delivered through the fuel line 18. In this preferred embodiment, a mixture of two liquid fuels, i.e., gasoline and alcohol (preferably methanol), is used, and the fuel mixture is specified by the weight percentage of one liquid fuel.

The flexible fuel system 10 includes a flexible fuel sensor 22, oscillator means 24 and output means 26. In this preferred embodiment, the sensor 22 is incorporated into the fuel line 18 to receive at least a portion of the liquid fuel mixture. The mixture flows through the sensor 22 (in the direction of the dotted arrows in FIG. 2) to the engine 14.

With particular reference to FIG. 2, the flexible fuel sensor 22 includes a first conductor 28 and a second conductor 30, positioned within the first conductor 28 in a substantially concentric arrangement. The first and second conductors 28, 30 are preferably cylindrical, coaxial and substantially equivalent in length. The liquid fuel mixture passes between the first and second conductors 28, 30 along a flowpath 32.

The first conductor 28 has first inlet and outlet ends 34, 36, respectively. The second conductor 30 has second inlet and outlet ends 38, 40, respectively. The second inlet and outlet ends 38, 40 are sealed by inlet and outlet plugs 42, 44, respectively. The inlet plug 42 is substantially flush with the second inlet end 38, whereas the plug 44 is displaced inwardly with respect to the second outlet end 40. The first and second conductors 28, 30 and the inlet and outlet plugs 42, 44 are preferably brass or stainless steel.

The concentric arrangement between the first and second conductors 28, 30 is maintained by inlet and outlet housings 46, 48, respectively. The inlet housing 46 includes an inlet coupling 50 for sealing engagement with the fuel line 18, such that the inlet housing 46 receives the liquid fuels.

The first inlet end 34 of the first conductor 28 is affixed and sealed to the inlet housing 46, opposite the inlet coupling 50. The second conductor 30 is positionally set by a retention plate or disc 52, having a central retention aperture 54 adapted to engagingly receive the second inlet end 38. In this preferred embodiment, the retention disc 52 is nonconductive so as to insulate the first conductor 28 from the second conductor 30. The retention disc 52 further includes a series of disc passageways 56, permitting fuel flow from the inlet coupling 50 to the flowpath 32. The retention disc 52 is secured within a substantially annular interior groove 58 in the inlet housing 46.

The outlet housing 48 includes an outlet coupling 60 and is adapted to receive and retain the first outlet end 36 of the first conductor 28. Within the outlet housing 48, the second outlet end 40 of the second conductor 30 is secured within a substantial annular channel 62, such that the inlet and outlet housings 46, 48 maintain the coaxial alignment of the first and second conductor 28, 30 and the substantially cylindrical flowpath 32.

The outlet housing 48 is conductive and electrically shorts the first and second outlet ends 36, 40 of the first and second conductors 28, 30, preferably to ground. The flexible fuel sensor 22 thus defines and provides a resonant electromagnetic cavity, generally designated 64, which resonates at a frequency dependent upon the fuel mixture, or more particularly the dielectric constant thereof.

The flexible fuel sensor 22 further includes drive and output terminals 66, 68, coupled to the oscillator means 24 and output means 26, respectively. The drive and output terminals 66, 68 are substantially opposed and extend through the inlet housing 46 for connection to the second conductor 30, or more particularly the inlet plug 42. The connection between the inlet plug 42 and drive terminal 66 is via a resistor 70.

The oscillator means 24 is, in this preferred embodiment, a fixed amplitude, fixed frequency oscillator 72. The preferred frequency range is 10 to 50 MHz. The oscillator 72 provides a driving voltage to the resonant cavity 64 of the flexible fuel cell 22, via the drive terminal 66 and resistor 70. In response, the output means 26 develops and provides a content signal representative of, or proportional to, the fuel mixture, i.e., the percentage by weight of methanol in the fuel line 18. In this preferred embodiment, the output means 26 is a resistor 74, interconnecting the output terminal 68 and ground, and the content signal is a voltage received by the electronic engine control 20.

Two advantages of the flexible fuel sensor 22 are simplicity of design and durability. These advantages reduce production and overall costs, a matter particularly critical in the automotive industry. The sensor 22 further reduces the adverse effects of parasitic inductance and resistance, thereby enhancing accuracy of the fuel mixture measurement.

Referring now to FIG. 3, a second preferred embodiment of the present invention is shown. The sensor 22 further includes a conventional peak detection circuit 76 and a ramp generator 78, interconnected as shown. The frequency of the oscillator means 24 is variable in a conventional fashion, and the oscillator frequency is substantially matched to the resonant frequency of the resonant electromagnetic cavity 64.

With engine start-up, the ramp generator 78 initiates a frequency sweep, i.e., a gradual increase in oscillator frequency, until a peak voltage from the output means 26 is detected by the peak detection circuit 76. At that point, the voltage output of the ramp generator 78 is correlated with the resonant frequency of the cavity 64 and constitutes the content signal provided to the engine control 20. Initiation of the frequency sweep at a low frequency (e.g., 10 MHz) substantially avoids detection of a "false" peak due resonant overtone modes.

The advantages of the preferred embodiment shown in FIG. 3 are accuracy and substantial avoidance of adverse measurement effects due to impurities (e.g., moisture and salts) in the fuel blend. The resonant frequency of the resonant cavity 64 is only slightly altered by the presence of such impurities, even at the maximum levels found in commercial fuels available throughout the United States.

Referring now to FIG. 4, another preferred embodiment of the present invention is shown. As is well known in the art, the fuel line 18 is coupled to a fuel rail 80 in close proximity with the engine 14. Typically the fuel rail 80 is stainless steel and heavier gauge than the fuel line 18. The fuel rail 80 includes a series of ports 82 for distribution of fuel to the fuel injectors (not shown).

In this preferred embodiment, the fuel rail 80 functions as the first conductor 28 of the flexible fuel sensor 22. The inlet and outlet housings 46, 48 interconnect the fuel line 18 to the inlet and outlet ends 84, 86, respectively, of the fuel rail 80. The second conductor 30, positionally retained by the inlet and outlet housings 46, 48, is a solid brass rod 88. Vibration of the solid second conductor 30 is substantially avoided, and isolation thereof from the fuel rail conductor 28 is maintained, by a series of nonconductive spacers 90.

The outlet end 86 of the fuel rail 80 and an outlet segment 92 of the solid conductor rod 88 are short-circuited, preferably to ground, by the outlet housing 48. An inlet segment 94 of the solid conductor rod 88 is secured within the inlet housing 46 in an insulating support 96. The inlet segment 94 is connected to a shielded electrical connector 98.

Various embodiments have been described herein. It is to be understood, however, that modifications and changes can be made without departing from the true scope and spirit of the present invention as defined by the following claims to be interpreted in light of the foregoing description.

What is claimed is:

1. A flexible fuel sensor for use in determining a fuel mixture of at least two liquid fuels comprising, in combination:

a first conductor having a first inlet end and a first outlet end;

a second conductor within said first conductor and having a second inlet end and a second outlet end, said liquid fuels flowing between said first and second conductors;

shorting means for electrically shorting said second outlet end of said second conductor to said first conductor;

an inlet housing for receiving said liquid fuels and for maintaining said second inlet end at a displaced position with respect to said first inlet end; and an outlet housing, providing said shorting means, for passing said liquid fuels and for shorting said first and second outlet ends;

said inlet and outlet housings retaining said first and second conductors in a substantially coaxial arrangement to define a flowpath between said first and second conductors and between said inlet and outlet housings, said liquid fuels flowing through said flowpath;

said flexible fuel sensor defining a resonant electromagnetic cavity having a resonant frequency dependent upon said fuel mixture.

2. A flexible fuel sensor as claimed in claim 1 further comprising drive and output terminals extending through said inlet housing and connected to said second inlet end of said second conductor.

3. A flexible fuel sensor as claimed in claim 2 wherein said drive terminal is connected to said second inlet end via a resistor.

4. A flexible fuel sensor as claimed in claim 3 wherein said inlet housing includes a retention plate to engage and positionally hold said second inlet end of said second conductor, said retention plate defining a passageway for said liquid fuels.

5. A flexible fuel sensor as claimed in claim 1 wherein said second outlet end of said second conductor defines a conductor passageway for said liquid fuels.

6. A flexible fuel sensor as claimed in claim 5 wherein said inlet housing includes a retention plate to engage and positionally hold said second inlet end of said second conductor, said retention plate defining a plate passageway for said liquid fuels.

7. A flexible fuel sensor as claimed in claim 2 or 1 wherein said first conductor forms a segment of a fuel rail.

* * * * *